(12) United States Patent
Burkinshaw et al.

(10) Patent No.: US 9,550,966 B2
(45) Date of Patent: *Jan. 24, 2017

(54) CLEANING METHOD

(71) Applicant: Xeros Limited, Rotherham (GB)

(72) Inventors: Stephen Martin Burkinshaw, West Yorkshire (GB); Stephen Derek Jenkins, Middlesborough (GB); Alan John Waddon, Sheffield (GB)

(73) Assignee: Xeros Limited, Rotherham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/809,650

(22) Filed: Jul. 27, 2015

(65) Prior Publication Data

US 2015/0344824 A1 Dec. 3, 2015

Related U.S. Application Data

(63) Continuation of application No. 13/822,339, filed as application No. PCT/GB2011/051727 on Sep. 14, 2011, now Pat. No. 9,121,000.

(30) Foreign Application Priority Data

Sep. 14, 2010 (GB) .................................. 1015277.5

(51) Int. Cl.
*C11D 3/12* (2006.01)
*C11D 3/37* (2006.01)
(Continued)

(52) U.S. Cl.
CPC ................. *C11D 3/48* (2013.01); *A01N 31/16* (2013.01); *A01N 59/16* (2013.01); *C11D 3/12* (2013.01);
(Continued)

(58) Field of Classification Search
CPC ............... C11D 3/12; C11D 3/37; C11D 3/48; C11D 11/0005; B08B 1/00
See application file for complete search history.

(56) References Cited

U.S. PATENT DOCUMENTS 2,970,464 A 2/1961 Toma
3,321,843 A 5/1967 Taran et al.
(Continued)

FOREIGN PATENT DOCUMENTS

CA 1284407 C 5/1991
CA 2147207 A 5/1994
(Continued)

OTHER PUBLICATIONS

U.S. Appl. No. 14/777,573, filed Sep. 16, 2015, Xeros Ltd.
(Continued)

*Primary Examiner* — Brian P Mruk
(74) *Attorney, Agent, or Firm* — Clark & Elbing LLP

(57) ABSTRACT

The invention provides a method and formulation for cleaning a soiled substrate, the method comprising the treatment of the moistened substrate with a formulation comprising a multiplicity of polymeric particles, wherein the polymeric particles comprise at least one antimicrobial agent. Preferably, the substrate is wetted so as to achieve a substrate to water ratio of between 1:0.1 to 1:5 w/w. Optionally, the formulation additionally comprises at least one additional cleaning agent, and in this embodiment, it is preferred that the polymeric particles are mixed with the at least one additional cleaning agent. Preferably, the additional cleaning material comprises a surfactant, which most preferably has detergent properties. Most preferably, the substrate comprises a textile fiber. Typically, the polymeric particles comprise particles of polyester or nylon, most preferably in the form of beads. The results obtained are very line with those observed when carrying out conventional aqueous (Continued)

cleaning processes and the method provides the significant advantage that the use of antimicrobial agents in or on the polymer bead greatly improves the overall hygiene in the washing machine by preventing mold and bacterial growth on the polymer particle surfaces, particularly at low temperatures.

19 Claims, 1 Drawing Sheet

(51) Int. Cl.
  *C11D 3/48* (2006.01)
  *B08B 1/00* (2006.01)
  *A01N 31/16* (2006.01)
  *A01N 59/16* (2006.01)
  *C11D 11/00* (2006.01)

(52) U.S. Cl.
  CPC ............... *C11D 3/128* (2013.01); *C11D 3/37* (2013.01); *C11D 3/3715* (2013.01); *C11D 3/3719* (2013.01); *C11D 3/3726* (2013.01); *C11D 3/3749* (2013.01); *C11D 11/0011* (2013.01); *C11D 11/0017* (2013.01)

(56) References Cited

U.S. PATENT DOCUMENTS

| | | | |
|---|---|---|---|
| 3,333,344 | A | 8/1967 | Loewen |
| 3,647,354 | A | 3/1972 | Loeb |
| 3,650,673 | A | 3/1972 | Ehner |
| 3,805,406 | A | 4/1974 | Castonoli |
| 4,055,248 | A | 10/1977 | Marsan |
| 4,130,392 | A | 12/1978 | Diehl et al. |
| 4,188,807 | A | 2/1980 | Graf et al. |
| 4,374,443 | A | 2/1983 | Mosell |
| 4,434,067 | A | 2/1984 | Malone et al. |
| 4,493,783 | A | 1/1985 | Su et al. |
| 4,575,887 | A | 3/1986 | Viramontes |
| 4,655,952 | A | 4/1987 | Mesmer et al. |
| 4,750,227 | A | 6/1988 | Hopkins et al. |
| 4,801,333 | A | 1/1989 | Mosell |
| 4,809,854 | A | 3/1989 | Tomaszek |
| 4,839,969 | A | 6/1989 | Hahn |
| 4,951,366 | A | 8/1990 | Geller |
| 4,978,619 | A | 12/1990 | Kajiwara et al. |
| 5,245,722 | A | 9/1993 | Dameron |
| 5,305,533 | A | 4/1994 | Alexander et al. |
| 5,367,734 | A | 11/1994 | Terry |
| 5,468,175 | A | 11/1995 | Nilen |
| 5,475,992 | A | 12/1995 | Wiegert |
| 5,503,840 | A | 4/1996 | Jacobson et al. |
| 5,547,476 | A | 8/1996 | Siklosi et al. |
| 5,601,480 | A | 2/1997 | Nilen |
| 5,605,491 | A | 2/1997 | Yam et al. |
| 5,667,431 | A | 9/1997 | Mortin |
| 5,804,548 | A | 9/1998 | Davis |
| 5,925,195 | A | 7/1999 | King et al. |
| 5,980,620 | A | 11/1999 | Brodie et al. |
| 5,993,839 | A | 11/1999 | Mixon |
| 6,235,705 | B1 | 5/2001 | Zembrodt et al. |
| 6,348,441 | B1 | 2/2002 | Aiken, III et al. |
| 6,376,046 | B1 | 4/2002 | Hoshino et al. |
| 6,448,212 | B1 | 9/2002 | Holderbaum et al. |
| 7,070,489 | B2 | 7/2006 | Rogmark |
| 7,097,715 | B1 | 8/2006 | Racette et al. |
| 7,481,893 | B2 | 1/2009 | Motson et al. |
| 7,498,294 | B2 | 3/2009 | Konno et al. |
| 8,959,961 | B2 | 2/2015 | Jenkins et al. |
| 8,974,545 | B2 * | 3/2015 | Burkinshaw ......... C11D 3/3719 8/137 |
| 9,017,423 | B2 * | 4/2015 | Burkinshaw ......... C11D 3/3719 8/137 |
| 9,121,000 | B2 * | 9/2015 | Burkinshaw ........... A01N 31/16 |
| 9,127,882 | B2 | 9/2015 | Jenkins et al. |
| 9,297,107 | B2 | 3/2016 | Jenkins |
| 2002/0010300 | A1 | 1/2002 | Mimoun |
| 2002/0016282 | A1 | 2/2002 | Kumar et al. |
| 2002/0039976 | A1 | 4/2002 | Sebillotte-Arnaud et al. |
| 2002/0058595 | A1 | 5/2002 | Kaiser |
| 2003/0110580 | A1 | 6/2003 | Burkinshaw et al. |
| 2003/0134759 | A1 | 7/2003 | Geary et al. |
| 2004/0171515 | A1 | 9/2004 | Hamers et al. |
| 2004/0266641 | A1 | 12/2004 | Gentschev et al. |
| 2005/0148479 | A1 | 7/2005 | Barthel et al. |
| 2005/0153865 | A1 | 7/2005 | Detering et al. |
| 2005/0183206 | A1 | 8/2005 | Brown et al. |
| 2005/0183208 | A1 | 8/2005 | Scheper et al. |
| 2005/0204477 | A1 | 9/2005 | Casella et al. |
| 2006/0287212 | A1 | 12/2006 | Sommer et al. |
| 2007/0151312 | A1 | 7/2007 | Bruce et al. |
| 2007/0270327 | A1 | 11/2007 | Beck et al. |
| 2008/0090746 | A1 | 4/2008 | Penninger |
| 2008/0223406 | A1 | 9/2008 | Lindqvist et al. |
| 2008/0276965 | A1 | 11/2008 | Aykroyd et al. |
| 2008/0306183 | A1 | 12/2008 | Leukel et al. |
| 2009/0090138 | A1 | 4/2009 | Wang |
| 2009/0186795 | A1 | 7/2009 | Feenstra et al. |
| 2009/0217461 | A1 | 9/2009 | Burkinshaw et al. |
| 2009/0276966 | A1 | 11/2009 | Mette et al. |
| 2010/0281928 | A1 | 11/2010 | Martin |
| 2011/0296628 | A1 | 12/2011 | Jenkins et al. |
| 2012/0048299 | A1 | 3/2012 | Jenkins et al. |
| 2012/0111359 | A1 | 5/2012 | Mueller et al. |
| 2012/0284931 | A1 | 11/2012 | Jenkins et al. |
| 2012/0304400 | A1 | 12/2012 | Jenkins et al. |
| 2013/0061404 | A1 | 3/2013 | Jenkins |
| 2013/0167882 | A1 | 7/2013 | Burkinshaw et al. |
| 2013/0276242 | A1 | 10/2013 | Jenkins et al. |
| 2013/0281345 | A1 | 10/2013 | Burkinshaw et al. |
| 2013/0283542 | A1 | 10/2013 | Jenkins et al. |
| 2013/0305560 | A1 | 11/2013 | Jenkins et al. |
| 2014/0137340 | A1 | 5/2014 | Burkinshaw et al. |
| 2015/0096128 | A1 | 4/2015 | Sawford et al. |
| 2015/0096129 | A1 | 4/2015 | Sawford et al. |
| 2015/0128358 | A1 | 5/2015 | Wells et al. |
| 2015/0148278 | A1 | 5/2015 | Burkinshaw et al. |
| 2015/0152357 | A1 | 6/2015 | Abercrombie et al. |
| 2015/0152585 | A1 | 6/2015 | Sawford et al. |
| 2015/0175945 | A1 | 6/2015 | Waddon et al. |
| 2015/0252511 | A1 | 9/2015 | Roberts et al. |
| 2016/0032522 | A1 | 2/2016 | Steele |
| 2016/0040260 | A1 | 2/2016 | Steele |
| 2016/0122932 | A1 | 5/2016 | Wells et al. |
| 2016/0122936 | A1 | 5/2016 | Wells et al. |

FOREIGN PATENT DOCUMENTS

| | | |
|---|---|---|
| CN | 2789299 Y | 6/2006 |
| CN | 101006108 A | 7/2007 |
| CN | 101886321 A | 11/2010 |
| CN | 102061588 A | 5/2011 |
| CN | 102061589 A | 5/2011 |
| CN | 202401272 U | 8/2012 |
| CN | 202500017 U | 10/2012 |
| CN | 202543635 U | 11/2012 |
| DE | 1900002 A1 | 7/1970 |
| DE | 2819233 A1 | 11/1979 |
| DE | 3527724 A1 | 2/1987 |
| DE | 3803195 A1 | 8/1989 |
| DE | 19505921 A1 | 8/1996 |
| DE | 10247289 A1 | 4/2004 |
| DE | 102008009462 A1 | 8/2009 |
| DE | 102009046170 A1 | 5/2011 |
| EP | 0090372 A1 | 10/1983 |
| EP | 0171215 A1 | 2/1986 |
| EP | 0312278 A2 | 4/1989 |
| EP | 0807463 A2 | 11/1997 |
| EP | 1371718 A1 | 12/2003 |
| FR | 2525645 A1 | 10/1983 |
| FR | 2826548 A1 | 1/2003 |
| GB | 1018318.4 | 1/1966 |
| GB | 920791 A | 3/1968 |

(56) References Cited

FOREIGN PATENT DOCUMENTS

| | | |
|---|---|---|
| GB | 1256064 A | 12/1971 |
| GB | 1297316 A | 11/1972 |
| GB | 1379742 A | 1/1975 |
| GB | 2249104 A | 4/1992 |
| GB | 2302553 A | 1/1997 |
| GB | 2365648 A | 2/2002 |
| GB | 2456407 A | 7/2009 |
| GB | 2473224 A | 3/2011 |
| JP | S59-48078 A | 3/1984 |
| JP | S59-196758 A | 11/1984 |
| JP | H01285188 A | 11/1989 |
| JP | H0257295 A | 2/1990 |
| JP | H03-146094 B2 | 6/1991 |
| JP | H04105633 A | 7/1992 |
| JP | H04241165 A | 8/1992 |
| JP | H06240297 A | 8/1994 |
| JP | 2004-167345 A | 6/2004 |
| JP | 2004238602 A | 8/2004 |
| JP | 2006-326434 A | 12/2006 |
| WO | WO-98/37270 A1 | 8/1998 |
| WO | WO-99/40251 A1 | 8/1999 |
| WO | WO-00/37540 A1 | 6/2000 |
| WO | WO-00/77153 A1 | 12/2000 |
| WO | WO-02/42403 A1 | 5/2002 |
| WO | WO-03/054128 A1 | 7/2003 |
| WO | WO-2004/066970 A1 | 8/2004 |
| WO | WO-2006/020789 A1 | 2/2006 |
| WO | WO-2006/040539 A1 | 4/2006 |
| WO | WO-2007/070520 A1 | 6/2007 |
| WO | WO 2007/128962 * 11/2007 .............. B08B 3/10 |
| WO | WO-2007/128962 A1 | 11/2007 |
| WO | WO-2008/132456 A1 | 11/2008 |
| WO | WO-2009/021919 A2 | 2/2009 |
| WO | WO-2009/112296 A1 | 9/2009 |
| WO | WO-2009/134018 A2 | 11/2009 |
| WO | WO-2010/046473 A1 | 4/2010 |
| WO | WO-2010/094959 A1 | 8/2010 |
| WO | WO-2010/128337 A2 | 11/2010 |
| WO | WO-2010/133837 A1 | 11/2010 |
| WO | WO-2010/139689 A1 | 12/2010 |
| WO | WO-2011/015429 A2 | 2/2011 |
| WO | WO-2011/051140 A1 | 5/2011 |
| WO | WO-2011/064581 A1 | 6/2011 |
| WO | WO-2011/098815 A1 | 8/2011 |
| WO | WO-2011/128676 A1 | 10/2011 |
| WO | WO-2011/128680 A2 | 10/2011 |
| WO | WO-2012/035342 A1 | 3/2012 |
| WO | WO-2012/056252 A2 | 5/2012 |
| WO | WO-2012/084619 A1 | 6/2012 |
| WO | WO-2012/095677 A2 | 7/2012 |
| WO | WO-2012/098408 A2 | 7/2012 |
| WO | WO-2012/104861 A1 | 8/2012 |
| WO | WO-2014/006424 A1 | 1/2014 |
| WO | WO-2014/006425 A1 | 1/2014 |
| WO | WO-2014/037729 A1 | 3/2014 |

OTHER PUBLICATIONS

U.S. Appl. No. 14/902,498, filed Dec. 31, 2015, Xeros Ltd.
U.S. Appl. No. 14/902,506, filed Dec. 31, 2015, Xeros Ltd.
U.S. Appl. No. 14/427,046, Xeros Ltd.
U.S. Appl. No. 14/588,500, Xeros Ltd.
U.S. Appl. No. 14/588,510, Xeros Ltd.
"Aqua Ball Set", <http://www.auravita.com/products/AURA/TAPR10610.asp>, retrieved on Aug. 14, 2006 (3 pages).
"Capture Carpet Cleaning Kit", <http://www.basichomeshopping.com/CaptureCarpetCleanerKit.html>, retrieved on Aug. 11, 2005 (4 pages).
"Capture Carpet Cleaning Kit", <http://www.domesticsale.com/Classifieds/15175.html>, retrieved on Aug. 11, 2005 (1 page).
International Preliminary Report on Patentability for International Application No. PCT/GB2011/051727, issued Mar. 19, 2013 (6 pages).
International Search Report for International Application No. PCT/GB2011/051727, mailed Dec. 22, 2011 (4 pages).
Michalon et al., "Enzyme coupling method on calibrated nylon spheres: application to the selective trypsinization of histones in chromatin," Biochem Biophys Res Commun. 167(1):9-15 (1990).
Migneault et al., "Glutaraldehyde: behavior in aqueous solution, reaction with proteins, and application to enzyme crosslinking," Biotechniques. 37(5):790-802 (2004).
Silva et al., "Laccase immobilization on enzymatically functionalized polyamide 6,6 fibres," Enzyme Microb Technol. 41:867-75 (2007).
Talbert et al., "Chitosan-tethered microspheres for lactase immobilization," J Mol Catal B Enzym. 78:78-84 (2012).
Written Opinion for International Application No. PCT/GB2011/051727, issued Mar. 14, 2013 (5 pages).

\* cited by examiner

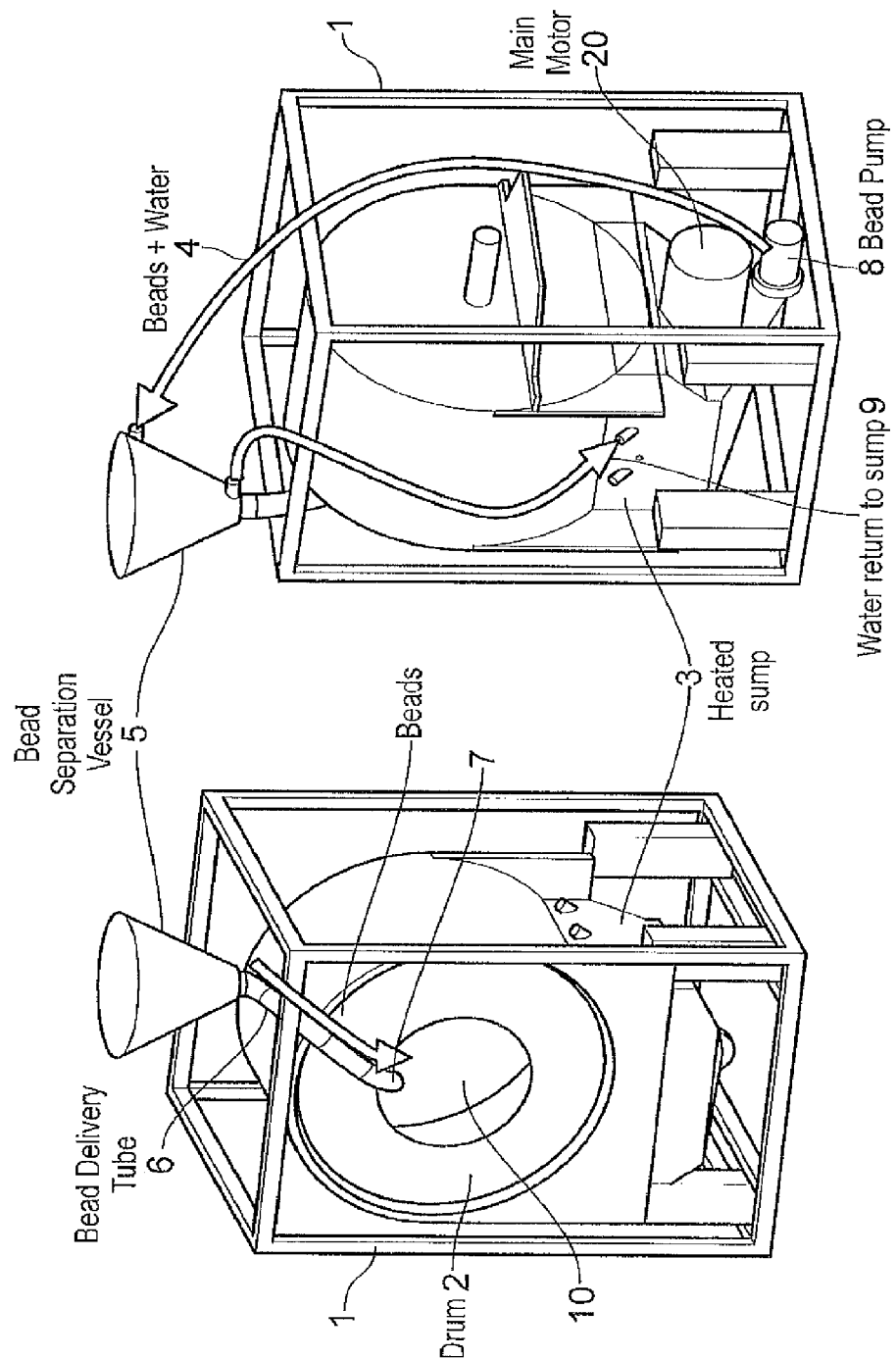

CLEANING METHOD

FIELD OF THE INVENTION

The present invention relates to the aqueous cleaning of soiled substrates, specifically textile fibres and fabrics, using a cleaning system comprising polymeric particles. More specifically, the invention is concerned with a system wherein the polymeric particles include antimicrobial agents which prevent mould and bacterial growth on the particles which may occur after repeated uses in washing procedures.

BACKGROUND TO THE INVENTION

Aqueous cleaning processes are a mainstay of both domestic and industrial textile fabric washing. On the assumption that the desired level of cleaning is achieved, the efficacy of such processes is usually characterised by their levels of consumption of energy, water and detergent. In general, the lower the requirements with regard to these three components, the more efficient the washing process is deemed. The downstream effect of reduced water and detergent consumption is also significant, as this minimises the need for disposal of aqueous effluent, which is both extremely costly and detrimental to the environment.

Such washing processes, whether in domestic washing machines or their industrial equivalents (usually referred to as washer extractors), involve aqueous submersion of fabrics followed by soil removal, aqueous soil suspension, and water rinsing. In general, the higher the level of energy (or temperature), water and detergent which is used, the better the cleaning. The key issue, however, concerns water consumption, as this sets the energy requirements (in order to heat the wash water), and the detergent dosage (to achieve the desired detergent concentration). In addition, the water usage level defines the mechanical action of the process on the fabric, which is another important performance parameter; this is the agitation of the cloth surface during washing, which plays a key role in releasing embedded soil. In aqueous processes, such mechanical action is provided by the water usage level, in combination with the drum design, for any particular washing machine. In general terms, it is found that the higher the water level in the drum, the better the mechanical action. Hence, there is a dichotomy created by the desire to improve overall process efficiency (i.e. the reduction of energy, water and detergent consumption), and the need for efficient mechanical action in the wash. For domestic washing in particular there are defined wash performance standards specifically designed to discourage the use of such higher levels in practice, in addition to the obvious cost penalties which are associated with such usage.

Current efficient domestic washing machines have made significant strides towards minimising their consumptions of energy, water and detergent. EU Directive 92/75/CEE sets a standard which defines washing machine energy consumption in kWh/cycle (cotton setting at 60° C.), such that an efficient domestic washing machine will typically consume <0.19 kWh/kg of washload in order to obtain an 'A' rating. If water consumption is also considered, then 'A' rated machines use <9.7 liters/kg of washload.

Detergent dosage is then driven by manufacturer recommendations but, again, in the domestic market, for a concentrated liquid formulation, a quantity of 35 ml (or 37 g) for a 4-6 kg washload in soft and medium hardness water, increasing to 52 ml (or 55 g) for a 6-8 kg washload (or in hard water or for very dirty items) is typical (see, for example, Unilever pack dosage instructions for Persil® Small & Mighty). Hence, for a 4-6 kg washload in soft/medium water hardness, this equates to a detergent dosage of 7.4-9.2 g/kg whilst, for a 6-8 kg washload (or in hard water or for very dirty items), the range is 6.9-9.2 g/kg.

Energy, water and detergent consumptions in the industrial washing process (washer-extractors) are considerably different, however, and usages of all three resources are less constrained, since these are the principal factors in reducing cycle time—which is, of course, more of a consideration than in the case of domestic use. For a typical industrial washer extractor (25 kg washload rated and above), energy consumption is 0.30-1.0 kWh/kg, water is at 20-30 liters/kg, and detergent is much more heavily dosed than for domestic washing. The exact level of detergent used will depend on the amount of soiling, but a range of 20-100 g/kg is representative.

Thus, it can be taken from the above discussion that it is the performance levels in the domestic sector which set the highest standard for an efficient fabric washing process, and that these are: an energy consumption of <0.19 kWh/kg, a water usage of <9.7 liters/kg, and a detergent dosage of approximately 8.0 g/kg. However, as previously observed, it is becoming increasingly difficult to reduce the water (and, hence, energy and detergent) levels in a purely aqueous process, due to the minimum requirement to wet the fabric thoroughly, the need to provide sufficient excess water to suspend the soil removed in an aqueous liquor and, finally, the necessity to rinse the fabric.

Heating of the wash water is then the principal use of energy, and a minimum level of detergent becomes necessary in order for an effective concentration to be reached at the operating wash temperature. Means to improve mechanical action without increasing the water level used would, therefore, make any aqueous wash process significantly more efficient (i.e. yield further reductions in energy, water and detergent consumption). It should be noted that mechanical action itself has a direct effect on the detergent level, since the greater the level of soil removal which is achieved through physical force, the less that is required of the detergent chemistry. However, increasing the mechanical action in a purely aqueous washing process has certain associated drawbacks. Fabric creasing readily occurs in such processes, and this acts to concentrate the stresses from mechanical action at each crease, resulting in localised fabric damage. Prevention of such fabric damage (i.e. fabric care) is of primary concern to the domestic consumer and the industrial user.

In the light of these challenges which are associated with aqueous washing processes, the present inventors have previously devised a new approach to the problem, which allows the deficiencies demonstrated by the methods of the prior art to be overcome. The method which is provided eliminates the requirement for the use of large volumes of water, but is still capable of providing an efficient means of cleaning and stain removal, whilst also yielding economic and environmental benefits.

Thus, in WO-A-2007/128962, there is disclosed a method and formulation for cleaning a soiled substrate, the method comprising the treatment of the moistened substrate with a formulation comprising a multiplicity of polymeric particles, wherein the formulation is free of organic solvents. Preferably, the substrate is wetted so as to achieve a substrate to water ratio of between 1:0.1 to 1:5 w/w, and optionally, the formulation additionally comprises at least one cleaning material, which typically comprises a surfactant, which most preferably has detergent properties. In preferred embodiments, the substrate comprises a textile fibre and the polymeric particles comprise, for example, particles of polyamides, polyesters, polyalkenes, polyurethanes or their copolymers but, most preferably, are in the form of nylon beads.

The use of this polymeric cleaning method, however, presents a requirement for the cleaning particles to be efficiently separated from the cleaned substrate at the conclusion of the cleaning operation, and this issue is addressed in WO-A-2010/094959, which provides a novel design of cleaning apparatus requiring the use of two internal drums capable of independent rotation, and which finds application in both industrial and domestic cleaning processes.

In co-pending WO-A-2011/064581, there is provided a further apparatus which facilitates efficient separation of polymeric cleaning particles from the cleaned substrate at the conclusion of the cleaning operation, and which comprises a perforated drum and a removable outer drum skin which is adapted to prevent the ingress or egress of fluids and solid particulate matter from the interior of the drum, the cleaning method requiring attachment of the outer skin to the drum during a wash cycle, after which the skin is removed prior to operating a separation cycle to remove the cleaning particles, following which the cleaned substrate is removed from the drum.

In a further development of the apparatus of WO-A-2011/064581, there is disclosed in co-pending WO-A-2011/098815 a process and apparatus which provides for continuous circulation of the polymeric cleaning particles during the cleaning process, and thereby dispenses with the requirement for the provision of an outer skin.

Further benefits in terms of reduced power and consumable requirements for the cleaning method originally proposed in WO-A-2007/128962 have been disclosed in co-pending GB Patent Application No. 1018318.4, where the technology has been refined to achieve at least equivalent cleaning performance whilst employing significantly reduced levels of detergents and much lower process temperatures.

The apparatus and methods disclosed in the foregoing prior art documents have been highly successful in providing an efficient means of polymeric cleaning and stain removal which also yields significant economic and environmental benefits. The move to much lower wash temperatures has been particularly beneficial in this regard. As a consequence of the achievement of such lower temperatures, however, the need to control hygiene in the washing machine has become significantly more important. Hotter wash temperatures (>60° C.) can provide some level of hygiene control via thermal disinfection, since heat is an efficient destroyer of mould and bacteria, and higher temperatures are increasingly beneficial. When these polymeric cleaning processes are run at lower temperatures (<40° C.), however, hygiene considerations are magnified compared to the equivalent aqueous process, due to the presence of the polymeric particles. Said particles provide a large additional surface area contained within the washing machine, on which mould and bacteria can grow. The growth here can be accelerated by the fact that the particles remain moist for a considerable time after each wash process has been run, and the overall levels of mould and bacteria reached can be further increased if the machine remains unused for extended periods of time.

The hygiene problem in the polymeric cleaning machine can, of course, be controlled by similar means to that used in conventional aqueous domestic or industrial washing, namely the use of higher wash temperatures as noted above, and/or chemical additives in the wash water used. Suitable additives include chlorine derived bleaches (e.g. sodium hypochlorite) or oxygen derived bleaches (e.g. hydrogen peroxide), but the use of these materials has drawbacks in that they can decolour some garment types, and generally promote fabric damage through chemical attack. The oxygen derived bleaches also become less effective at lower wash temperatures (<40° C.), even when used in combination with suitable activators, e.g tetraacetyl ethylene diamine. Other additives based on chloro compounds (e.g. liquid chlorophenols) can also be used, but with similar drawbacks. Possibly the most benign means of achieving antimicrobial performance in the wash water is via the addition of silver-containing materials (e.g. silver-containing zeolite materials). Such approaches are expensive to consider, however, as they are effectively applicable for single wash use only. Furthermore, as in all cases with chemical additives in the wash water, there are effluent treatment considerations to take into account.

In looking to further develop the method of the cleaning process from WO-A-2007/128962 and co-pending GB Patent Application No. 1018318.4, therefore, the present inventors have now sought to provide a process which allows the aforementioned hygiene deficiencies with polymeric cleaning to be overcome, particularly at low wash temperatures (<40° C.). Hence, in the presently claimed invention, the inventors, by means of the addition of an antimicrobial agent to the polymeric particles, seek to provide a process in which lower levels of mould and bacterial growth occur within the washing machine at all times. The introduction of the antimicrobial agent in this way overcomes the drawbacks which would be associated with single use addition into the wash water (i.e. fabric damage, expense and effluent treatment considerations), and the action of the antimicrobial agent is continuous over the lifetime of the polymeric particles, which are re-used many times in subsequent washes, as is common practice with this technology.

STATEMENT OF INVENTION

Thus, according to a first aspect of the present invention, there is provided a method for aqueous cleaning of soiled substrates, said method comprising the treatment of the moistened substrate with a formulation comprising a multiplicity of polymeric particles, wherein said polymeric particles comprise at least one antimicrobial agent.

Said substrate may comprise any of a wide range of substrates, including, for example, plastics materials, leather, paper, cardboard, metal, glass or wood. In practice, however, said substrate most preferably comprises a textile fibre or fabric, which may comprise either a natural material, such as cotton, or a synthetic textile material, for example nylon 6,6 or a polyester.

Said antimicrobial agent inhibits the growth of microbes such as mould and bacteria, and may comprise any readily commercially available product which is suitable for such purposes, and which would be well known to the skilled person. Particularly suitable agents include solid chlorophenol derivatives, such as 5-chloro-2-(2,4-dichlorophenoxy) phenol, which is commercially available as Triclosan or Microban®, or its derivatives, and silver-containing materials, most particularly silver-containing zeolite materials, including products from the Bio-Gate™ Irgaguard® or HyGate™ ranges including, for example, Bio-Gate™ BG-Tec Plus, Irgaguard® B 5000, Irgaguard® B 7000, HyGate™ 4000 and HyGate™ 9000.

Said polymeric particles may comprise any of a wide range of different polymers. Specifically, there may be mentioned polyalkenes such as polyethylene and polypropylene, polyesters and polyurethanes. Preferably, however, said polymeric particles comprise polyester or polyamide particles, most particularly particles of polyethylene terephthalate, polybutylene terephthalate, nylon 6, and nylon 6,6, most preferably in the form of beads. Said polyesters and polyamides are found to be particularly effective for aqueous stain/soil removal, whilst polyalkenes are especially useful for the removal of oil-based stains. Optionally, copolymers of the above polymeric materials may be employed for the purposes of the invention.

Specifically, the properties of the polymeric materials may be tailored to particular requirements by the inclusion of monomeric units which confer desired properties on the copolymer. Thus, the polymers may be adapted to attract particular staining materials by comprising co-monomers which, inter alia, are ionically charged, or include polar moieties or unsaturated organic groups. Examples of such groups may include, for example, acid or amino groups, or salts thereof, or pendant alkenyl groups.

Furthermore, the polymeric particles may comprise either foamed or unfoamed polymeric materials. Additionally, the polymeric particles may comprise polymers which are either linear or crosslinked, and said particles may be solid or hollow.

Said antimicrobial agent is most conveniently introduced into said polymer particles during extrusion of said polymer. Thus, the antimicrobial agent is especially preferably added to the molten polymer prior to extrusion. In an alternative embodiment, said polymer particles may be coated with said antimicrobial agent after extrusion.

Preferably, said antimicrobial agent is added to said polymer at a level of 0.1-5.0%, (w/w), most preferably 0.5-2.5% (w/w), especially preferably 1.5-2.0% (w/w).

Whilst, in one embodiment, the method of the invention envisages the cleaning of a soiled substrate by the treatment of a moistened substrate with a formulation which essentially consists only of a multiplicity of polymeric particles which comprise at least one antimicrobial agent, in the absence of any further additives, optionally in other embodiments the formulation employed may further comprise at least one additional cleaning agent. Preferably, the at least one additional cleaning agent comprises at least one surfactant. Preferred surfactants comprise surfactants having detergent properties and said additional cleaning agents preferably comprise detergent formulations. Said surfactants may comprise anionic, non-ionic, cationic, ampholytic, zwitterionic and/or semi-polar non-ionic surfactants. Optionally, said at least one additional cleaning agent comprises at least one enzyme and/or bleach. Preferably, said at least one additional cleaning agent is mixed with said polymeric particles but, in an alternative embodiment, each of said polymeric particles is coated with said at least one additional cleaning agent. Further additives may be incorporated with said additional cleaning agent, as appropriate; said additives may include, for example, anti-redeposition additives, optical brighteners, perfumes, softeners and starch, which can enhance the appearance and other properties of the cleaned substrate.

As previously stated, various polyester and/or polyamide homo- or co-polymers may be used for the polymeric particles, including polyethylene terephthalate, polybutylene terephthalate, nylon 6 and nylon 6,6. Preferably, the nylon comprises nylon 6,6 homopolymer having a molecular weight in the region of from 5000 to 30000 Daltons, preferably from 10000 to 20000 Daltons, most preferably from 15000 to 16000 Daltons. The polyester will typically have a molecular weight corresponding to an intrinsic viscosity measurement in the range of from 0.3-1.5 dl/g as measured by a solution technique such as ASTM D-4603.

The ratio of polymeric particles to substrate is generally in the range of from 0.1:1 to 10:1 w/w, preferably in the region of from 0.5:1 to 5:1 w/w, with particularly favourable results being achieved with a ratio of between 1:1 and 3:1 w/w, and especially at around 2:1 w/w. Thus, for example, for the cleaning of 5 g of substrate, typically textile fabric, 10 g of polymeric particles, optionally coated with surfactant, would be employed in one embodiment of the invention. The ratio of polymeric particles to substrate is maintained at a substantially constant level throughout the wash cycle.

The polymeric particles are of such a shape and size as to allow for good flowability and intimate contact with the soiled substrate, which typically comprises a textile fibre or fabric. A variety of shapes of particles can be used, such as cylindrical, spherical or cuboid; appropriate cross-sectional shapes can be employed including, for example, annular ring, dog-bone and circular. In preferred embodiments of the invention, said particles are in the form of beads and, most preferably, comprise cylindrical or spherical beads.

The particles may have smooth or irregular surface structures and can be of solid or hollow construction. Particles are of such a size as to have an average mass of 1-50 mg, preferably from 10-30 mg, more preferably from 12-25 mg.

In the case of cylindrical beads, the preferred particle diameter is in the region of from 1.0 to 6.0 mm, more preferably from 1.5 to 4.0 mm, most preferably from 2.0 to 3.0 mm, and the length of the beads is preferably in the range from 1.0 to 5.0 mm, more preferably from 1.5 to 3.5 mm, and is most preferably in the region of 2.0 to 3.0 mm.

Typically, for spherical beads, the preferred diameter of the sphere is in the region of from 1.0 to 6.0 mm, more preferably from 2.0 to 4.5 mm, most preferably from 2.5 to 3.5 mm.

The method of the invention may be applied to a wide variety of substrates, as previously stated. More specifically, it is applicable across the range of natural and synthetic textile fibres and fabrics, but it finds particular application in respect of nylon 6,6, polyester and cotton fabrics.

Prior to treatment according to the method of the invention, the substrate is moistened by wetting with water, to provide additional lubrication to the cleaning system and thereby improve the transport properties within the system. Thus, more efficient transfer of the at least one cleaning material to the substrate is facilitated, and removal of soiling and stains from the substrate occurs more readily. Most conveniently, the substrate may be wetted simply by contact with mains or tap water. Preferably, the wetting treatment is carried out so as to achieve a substrate to water ratio of between 1:0.1 to 1:5 w/w; more preferably, the ratio is between 1:0.2 and 1:2, with particularly favourable results having been achieved at ratios such as 1:0.2, 1:1, 1:1.2 and 1:2. However, in some circumstances, successful results can be achieved with substrate to water ratios of up to 1:50, although such ratios are not preferred in view of the significant amounts of effluent which are generated.

Suitable examples of apparatus for the execution of this method are disclosed in WO-A-2010/094959, WO-A-2011/064581 and WO-A-2011/098815. In preferred embodiments of the invention, the claimed method additionally provides for separation and recovery of the polymeric particles, which are then re-used in subsequent washes.

As a consequence of employing the cleaning method of the present invention, excellent cleaning performance may be achieved whilst using significantly reduced levels of detergents and much lower process temperatures. Thus, cleaning operations according to the invention, whilst possible at temperatures up to 95° C., are typically carried out at temperatures not exceeding 65° C., and optimum performance is generally achieved at 5-35° C. It is at this lower end of the operational temperature range that the antimicrobial polymeric particles ensure improved hygiene in the washing machine used.

According to a second aspect of the present invention, there is provided a formulation for aqueous cleaning of soiled substrates, said formulation comprising a multiplicity of polymeric particles, wherein said polymeric particles comprise at least one antimicrobial agent.

Said substrate may comprise any of a wide range of substrates, including, for example, plastics materials, leather, paper, cardboard, metal, glass or wood. In practice, however, said substrate most preferably comprises a textile fibre or fabric, which may comprise either a natural material, such as cotton, or a synthetic textile material, for example nylon 6,6 or a polyester.

In one embodiment, said formulation may essentially consist only of said multiplicity of polymeric particles which comprise at least one antimicrobial agent, but optionally in other embodiments said formulation further comprises at least one additional cleaning agent. Preferably, the at least one additional cleaning agent comprises at least one surfactant. Preferred surfactants comprise surfactants having detergent properties and said additional cleaning agents preferably comprise detergent formulations. Said surfactants may comprise anionic, non-ionic, cationic, ampholytic, zwitterionic, and/or semi-polar non-ionic surfactants. Optionally, said at least one additional cleaning agent also comprises at least one enzyme and/or bleach.

Said formulation is preferably used in accordance with the method of the first aspect of the invention, and is as defined in respect thereof. Additional additives may be incorporated in said formulation, as appropriate; said additives may include, for example, anti-redeposition additives, optical brighteners, perfumes, softeners and starch which can enhance the appearance and other properties of the cleaned substrate.

The formulation and the method of the present invention may be used for either small or large scale processes of both the batchwise and continuous variety and, therefore, find application in both domestic and industrial cleaning processes. Excellent performance can also result from the use of fluidised beds, and this is particularly the case when the method of the invention is used for carrying out wet cleaning processes.

BRIEF DESCRIPTION OF THE DRAWINGS

Embodiments of the invention are further described hereinafter with reference to the accompanying drawings, in which:

FIGS. 1(a) and (b) show an apparatus suitable for use in the performance of the method of the invention.

DETAILED DESCRIPTION OF THE INVENTION

As previously noted, the antimicrobial agent is most conveniently introduced into the polymer particles during extrusion of said polymer and is then added in a suitable amount to the molten polymer prior to extrusion. Particularly suitable agents include solid chlorophenol derivatives, such as 5-chloro-2-(2,4-dichlorophenoxy)phenol, which is commercially available as Triclosan or Microban®, or its derivatives, and silver-containing materials, including products from the Bio-Gate™, Irgaguard® or HyGate™ ranges including, for example, Bio-Gate™ BG-Tec Plus, Irgaguard® B 5000, Irgaguard® B 7000, HyGate™ 4000 and HyGate™ 9000. Preferably, said antimicrobial agent is added to said polymer at a level of 0.1-5.0%, (w/w), most preferably 0.5-2.5% (w/w), especially preferably 1.5-2.0% (w/w).

In alternative embodiments, the polymer particles may be coated with the antimicrobial agent after extrusion in which case the particles are suitably placed in a container with an appropriate amount of the antimicrobial agent, and the preferably sealed container is agitated for, typically, 15-30 minutes at temperatures at or just above ambient temperature. The coated particles are then removed from the container and are ready for use in cleaning processes.

In a typical operation of a cleaning cycle according to the method of the invention, soiled garments are first placed into a rotatably mounted cylindrical cage of a cleaning apparatus according to the method described in WO-A-2011/098815. Such an apparatus is illustrated in FIGS. 1(a) and 1(b), wherein there is seen an apparatus comprising housing means (1) having a first upper chamber having mounted therein a rotatably mounted cylindrical cage in the form of drum (2) (perforations not shown) and a second lower chamber comprising sump (3) located beneath said cylindrical cage. The apparatus additionally comprises, as first recirculation means, bead and water riser pipe (4) which feeds into separating means comprising a bead separation vessel (5), including filter material, typically in the form of a wire mesh, and a bead release gate valve which feeds into feeder means comprising bead delivery tube (6) mounted in cage entry (7). The first recirculation means is driven by pumping means comprising bead pump (8). Additional recirculation means comprises return water pipe (9), which allows water to return from the bead separation vessel (5) to the sump (3) under the influence of gravity. The apparatus also comprises access means shown as loading door (10), though which material for cleaning may be loaded into drum (2). The main motor (20) of the apparatus, responsible for driving the drum (2), is also depicted.

Following loading of the soiled garments into said apparatus, the polymeric particles and the necessary amount of water, together with any required additional cleaning agent, are added to said rotatably mounted cylindrical cage (2). Optionally, said materials are introduced via the first recirculation means (4) into the cylindrical cage (2), which is located in a first chamber of said apparatus. Alternatively, said polymeric particles may, for example, be pre-mixed with water and added via the separating means (5) located adjacent said cylindrical cage (2).

During the course of agitation by rotation of the cage (2), the fluids and a quantity of the polymeric particles exit through perforations in the cage (2) and into the second chamber (3) of the apparatus. Thereafter, the polymeric particles may be recirculated via the first recirculation means (4) such that they are transferred to the separating means (5), from which they are returned, in a manner controlled by control means, to the cylindrical cage (2) for continuation of the washing operation. This process of continuous circulation of the polymeric particles continues throughout the washing operation until cleaning is completed.

Thus, the polymeric particles which exit through the perforations in the walls of said rotatably mounted cylindrical cage (2) and into said second chamber (3) are recirculated and reintroduced through said separation means (5) and, by operation of control means, through the feeder means (6), back into said cage (2), thereby to continue the cleaning operation.

Typically, a wash cycle according the method of the present invention comprises the steps of:
(a) introducing polymeric particles, additional cleaning agent and water into a second chamber of a cleaning apparatus of the type described in WO-A-2011/098815;
(b) agitating said polymeric particles, additional cleaning agent and water;
(c) loading at least one soiled substrate into the rotatably mounted cylindrical cage of said apparatus via access means;
(d) closing the access means so as to provide a substantially sealed system;
(e) introducing said polymeric particles, additional cleaning agent and water into said rotatably mounted cylindrical cage;
(f) operating the apparatus for a wash cycle, wherein said rotatably mounted cylindrical cage is caused to rotate and wherein fluids and polymeric particles are caused to fall through perforations in said rotatably mounted cylindrical cage into said second chamber in a controlled manner;
(g) operating pumping means so as to transfer fresh polymeric particles and recycle used polymeric particles to separating means;
(h) operating control means so as to add said fresh and recycled polymeric particles to said rotatably mounted cylindrical cage in a controlled manner; and
(i) continuing with steps (f), (g) and (h) as required to effect cleaning of the soiled garments.

Optionally, said polymeric particles, additional cleaning agent and water may be introduced into said rotatably mounted cylindrical cage via recirculating means. More preferably, however, said polymeric particles, additional cleaning agent and water are introduced into said rotatably mounted cylindrical cage via dosing means such as, for example, a fixedly mounted nozzle. Most conveniently, said nozzle may be fixedly mounted on said access means.

Additional cleaning agents are advantageously employed in said method, as further discussed below. Said additional cleaning agents may be added to the second chamber of said apparatus with said polymeric particles and introduced, via the first recirculation means, into the cylindrical cage. Alternatively, an additional cleaning agent is pre-mixed with water and added to said cylindrical cage via the separating means during step (e). More preferably, however, said additional cleaning agents are added to said cylindrical cage via said dosing means. The method of the invention facilitates the use of reduced quantities of said additional cleaning agents.

In preferred embodiments of the invention, said additional cleaning agents may be added to said cylindrical cage in multiple dosing steps during the cleaning operation, rather than in a single dosing step.

Preferably, pumping of said fresh and recycled polymeric particles proceeds at a rate sufficient to maintain approximately the same level of particles in said rotatably mounted cylindrical cage throughout the cleaning operation, and to ensure that the ratio of particles to soiled garments stays substantially constant until the wash cycle has been completed.

On completion of the wash cycle, feeding of polymeric particles into the rotatably mounted cylindrical cage ceases and the speed of rotation of the cage is gradually increased in order to effect a measure of drying of the cleaned substrate. Some polymeric particles are removed at this stage. Typically, the cage is rotated at a rotation speed of between 100 and 800 rpm in order to achieve drying; for a 98 cm diameter cage, a suitable speed of rotation would be around 300 rpm. Subsequently, rotation speed is reduced and returned to the speed of the wash cycle, so as to allow for final removal of the polymeric particles. After separation, the polymeric particles are recovered in order to allow for re-use in subsequent washes.

Optionally, following initial drying at high rpm, said method may additionally comprise a rinsing operation, wherein additional water may be added to said rotatably mounted cylindrical cage in order to effect complete removal of any additional cleaning agent employed in the cleaning operation. Water may be added to said cylindrical cage via said separating means, by said dosing means, or by overfilling the second chamber of said apparatus with water such that it enters the first chamber and thereby enters into said rotatably mounted cylindrical cage. Following rotation at the same speed as during the wash cycle, water is removed from said cage by allowing the water level to fall, as appropriate, and again increasing the speed of rotation to, typically, 100-800 rpm in order to achieve a measure of drying of the substrate; a speed of rotation of around 300 rpm would, once again, be appropriate for a 98 cm diameter cage. Said rinsing and drying cycles may be repeated as often as desired.

Optionally, said rinse cycle may be used for the purposes of substrate treatment, involving the addition of treatment agents such as anti-redeposition additives, optical brighteners, perfumes, softeners and starch to the rinse water.

Said polymeric particles are preferably subjected to a cleaning operation in said second chamber by sluicing said chamber with clean water in the presence or absence of a cleaning agent, which may be selected from at least one of surfactants, enzymes and bleaches. Alternatively, cleaning of the polymeric particles may be achieved as a separate stage in said rotatably mounted cylindrical cage. After cleaning, the polymeric particles are recovered such that they are available for use in subsequent washes.

Generally, any remaining polymeric particles on said garments may be easily removed by shaking the garments. If necessary, however, further remaining polymeric particles may be removed by suction means, preferably comprising a vacuum wand.

The method of the invention is principally applied to the cleaning of substrates comprising textile fibres and fabrics, and has been shown to be particularly successful in achieving efficient cleaning of textile fabrics which may, for example, comprise either natural materials, such as cotton, or man-made and synthetic textile materials, for example nylon 6,6, polyester, cellulose acetate, or fibre blends thereof.

The volume of wash water added to the system is calculated so as to achieve a fabric to wash water ratio which is preferably between 1:0.1 and 1:5 w/w; more preferably, the ratio is between 1:0.2 and 1:2, with particularly favourable results having been achieved at ratios such as 1:0.2, 1:1, 1:1.2 and 1:2. Most conveniently, the required amount of water is introduced into the rotatably mounted cylindrical cage of the apparatus after loading of the soiled substrate into said cage. An additional amount of water will migrate into the cage during the circulation of the polymeric particles, but the amount of water carry over is minimised by the action of the separating means.

As previously stated, preferred embodiments of the method of the invention envisage the cleaning of soiled textile fibres or fabrics by treatment of the moistened fibres or fabrics with a formulation which include a multiplicity of polymeric particles and further comprise at least one additional cleaning agent. Said at least one additional cleaning agent preferably comprises at least one detergent composition.

The principal components of the detergent composition comprise cleaning components and post-treatment components. Typically, the cleaning components comprise surfactants, enzymes and bleach, whilst the post-treatment components include, for example, anti-redeposition additives, optical brighteners, perfumes, softeners and starch.

However, the detergent composition may optionally include one or more other additives such as, for example builders, chelating agents, dye transfer inhibiting agents, dispersants, enzyme stabilizers, catalytic materials, bleach activators, polymeric dispersing agents, clay soil removal agents, suds suppressors, dyes, structure elasticizing agents, fabric softeners, starches, carriers, hydrotropes, processing aids and/or pigments.

Examples of suitable surfactants may be selected from non-ionic and/or anionic and/or cationic surfactants and/or ampholytic and/or zwitterionic and/or semi-polar nonionic surfactants. The surfactant may be present at a level of from about 0.1% to about 99.9% by weight of the cleaning composition, but is usually present from about 1% to about 80%, more typically from about 5% to about 35%, or from about 5% to 30% by weight of the cleaning compositions.

The detergent composition may include one or more detergent enzymes which provide cleaning performance and/or fabric care benefits. Examples of suitable enzymes include, but are not limited to, hemicellulases, peroxidases, proteases, other cellulases, other xylanases, lipases, phospholipases, esterases, cutinases, pectinases, keratanases, reductases, oxidases, phenoloxidases, lipoxygenases, ligninases, pullulanases, tannases, pentosanases, malanases, [beta]-glucanases, arabinosidases, hyaluronidase, chondroitinase, laccase, and amylases, or mixtures thereof. A typical combination may comprise a mixture of enzymes such as protease, lipase, cutinase and/or cellulase in conjunction with amylase.

Optionally, enzyme stabilisers may also be included amongst the cleaning components. In this regard, enzymes for use in detergents may be stabilised by various techniques, for example by the incorporation of water-soluble sources of calcium and/or magnesium ions in the compositions.

The detergent composition may include one or more bleach compounds and associated activators. Examples of such bleach compounds include, but are not limited to, peroxygen compounds, including hydrogen peroxide, inorganic peroxy salts, such as perborate, percarbonate, perphosphate, persilicate, and monopersulphate salts (e.g. sodium perborate tetrahydrate and sodium percarbonate), and organic peroxy acids such as peracetic acid, monoperoxyphthalic acid, diperoxydodecanedioic acid, N,N'-terephthaloyl-di(6-aminoperoxycaproic acid), N,N'-phthaloylaminoperoxycaproic acid and amidoperoxyacid. Bleach activators include, but are not limited to, carboxylic acid esters such as tetraacetylethylenediamine and sodium nonanoyloxybenzene sulfonate.

Suitable builders may be included in the formulations and these include, but are not limited to, the alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

The detergent composition may also optionally contain one or more copper, iron and/or manganese chelating agents and/or one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof.

Optionally, the detergent formulation can also contain dispersants. Suitable water-soluble organic materials are the homo- or co-polymeric acids or their salts, in which the polycarboxylic acid may comprise at least two carboxyl radicals separated from each other by not more than two carbon atoms.

Suitable anti-redeposition additives are physico-chemical in their action and include, for example, materials such as polyethylene glycol, polyacrylates and carboxy methyl cellulose.

Optionally, the detergent composition may also contain perfumes. Suitable perfumes are generally multi-component organic chemical formulations, a suitable example of which is Amour Japonais supplied by Symrise® AG.

Appropriate optical brighteners fall into several organic chemical classes, of which the most popular are stilbene derivatives, whilst other suitable classes include benzoxazoles, benzimidazoles, 1,3-diphenyl-2-pyrazolines, coumarins, 1,3,5-triazin-2-yls and naphthalimides. Examples of such compounds include, but are not limited to, 4,4'-bis[[6-anilino-4(methylamino)-1,3,5-triazin-2-yl]amino]stilbene-2,2'-disulfonic acid, 4,4'-bis[[6-anilino-4-[(2-hydroxyethyl)methylamino]-1,3,5-triazin-2-yl]amino]stilbene-2,2'-disulphonic acid, disodium salt, 4,4'-Bis[[2-anilino-4-[bis(2-hydroxyethyl)amino]-1,3,5-triazin-6-yl]amino]stilbene-2,2'-disulfonic acid, disodium salt, 4,4'-bis[(4,6-dianilino-1,3,5-triazin-2-yl)amino]stilbene-2,2'-disulphonic acid, disodium salt, 7-diethylamino-4-methylcoumarin, 4,4'-Bis[(2-anilino-4-morpholino-1,3,5-triazin-6-yl)amino]-2,2'-stilbenedisulfonic acid, disodium salt, and 2,5-bis(benzoxazol-2-yl)thiophene.

Said agents may be used either alone or in any desired combination and may be added to the cleaning system at appropriate stages during the cleaning cycle in order to maximise their effects.

The method of the present invention may be used for either small or large scale batchwise or continuous processes and finds application in both domestic and industrial cleaning processes.

As previously noted, the method of the invention finds particular application in the cleaning of textile fibres and fabrics. The conditions employed in such a cleaning system do, however, allow the use of significantly reduced temperatures from those which typically apply to the conventional wet cleaning of textile fibres and fabrics and, as a consequence, offer significant environmental and economic benefits. Thus, typical procedures and conditions for the wash cycle require that fibres and fabrics are generally treated according to the method of the invention at, for example, temperatures of between 5 and 35° C. for a duration of between 5 and 45 minutes, optimally in a substantially sealed system. Thereafter, additional time is required for the completion of the rinsing and bead separation stages of the overall process, so that the total duration of the entire cycle is typically in the region of 1 hour.

It is at these lower wash temperatures that the efficacy of the presently claimed invention is greatest. The inventors have sought, by addition of an antimicrobial agent to the polymeric particles used, to provide a process in which lower levels of mould and bacterial growth occur in the washing machine at all times. The introduction of the antimicrobial agent in this way, overcomes the drawbacks associated with single use addition into the wash water (i.e. fabric damage, expense and effluent treatment considerations), and its action is continuous over the lifetime of the polymeric particles, as said particles are re-used many times in subsequent washes, as is common practice with this technology.

The invention will now be further illustrated, though without in any way limiting the scope thereof, by reference to the following examples and associated illustrations.

EXAMPLE

Approximately 80 kg of nylon 6,6 beads were supplied by Rhodia Operations, Aubervilliers, France—grade 24FE3. This material was divided into individual samples of approximately 20 kg, each of which was then dried for 3% hours at 80° C. in a desiccator. The polymer beads and the appropriate amounts of a silver zeolite antimicrobial agent (Bio Gate™ BG-Tec Plus) when used, were intimately mixed by shaking them together in a sealed container, prior to extrusion using a Rondol 21 mm diameter twin screw extruder at Smithers-RAPRA, Shawbury, UK. The four samples of polymer beads produced contained 0% (as a control, comparative example), and 1.0, 1.5 and 2.0% w/w levels of the Bio Gate™ BG-Tec Plus respectively. The twin screw extruder was operated with a screw speed of 400 rpm, and with 8 sequential temperature settings down the barrel, namely: zone 1 @ 240° C., zone 2 @ 250° C., zone 3 @ 260° C., zone 4 @ 265° C., zone 5 @ 265° C., zone 6 @ 265° C., and zone 7 @ 265° C. The die plate (zone 8) was also maintained at 265° C. The extruded lace was then passed through a water bath to cool and form a continuous solid strand, before being cut to form polymer beads of approximate dimensions 4.0×1.7×1.7 mm.

In order to test the antimicrobial efficiency of these beads, 25 g aliquots of each bead sample were inoculated with 6 ml of either *pseudomonas aeruginosa* (pa) at approximately $3.1 \times 10^3$ cfu/ml (colony forming units/milliliter), or *aspergillus brasiliensis* (ab) at approximately $1.4 \times 10^3$ cfu/ml. The inoculated beads were then stored at $(31\pm1)°$ C. for the duration of the study, and at various time points (t), samples of the beads representing 1 ml of the inoculum (i.e. 5.17 g of beads/inoculum mixture) were removed to 9 ml of diluent and shaken vigorously. The resulting suspensions were tested using a standard plate count method. Incubation was for 5 days at $(31\pm1)°$ C. for the pa based suspensions in tryptone soya agar growth medium, and for 5 days at $(24\pm1)°$ C. for the ab based suspensions in sabouraud dextrose agar growth medium. The results are shown in Table 1.

TABLE 1 pa and ab cfu/ml Results for the Inoculated Bead Samples

| Bead Sample | Count (cfu/ml) at t = 0 | Count (cfu/ml) at t = 24 hours | Count (cfu/ml) at t = 4 days | Count (cfu/ml) at t = 7 days | Count (cfu/ml) at t = 14 days |
|---|---|---|---|---|---|
| 24FE3 control | pa = $3.1 \times 10^3$<br>ab = $1.4 \times 10^3$ | pa = >$10^6$<br>ab = $1.5 \times 10^3$ | pa = >$10^6$<br>ab = Not Measured | pa = >$10^6$<br>ab = $2.1 \times 10^4$ | pa = >$10^6$<br>ab = $1.8 \times 10^4$ |
| 24FE3 + 1.0% w/w BG-Tec Plus | pa = $3.1 \times 10^3$<br>ab = $1.4 \times 10^3$ | pa = $1.3 \times 10^5$<br>ab = $1.5 \times 10^3$ | pa = >$10^6$<br>ab = Not Measured | pa = >$10^6$<br>ab = $1.4 \times 10^2$ | pa = >$10^6$<br>ab = 10 |
| 24FE3 + 1.5% w/w BG-Tec Plus | pa = $3.1 \times 10^3$<br>ab = $1.4 \times 10^3$ | pa = $2.1 \times 10^5$<br>ab = $1.3 \times 10^3$ | pa = $5.3 \times 10^5$<br>ab = Not Measured | pa = $3.6 \times 10^5$<br>ab = $1.6 \times 10^2$ | pa = >$10^6$<br>ab = <10 |
| 24FE3 + 2.0% w/w BG-Tec Plus | pa = $3.1 \times 10^3$<br>ab = $1.4 \times 10^3$ | pa = <10<br>ab = $1 \times 10^3$ | pa = <10<br>ab = Not Measured | pa = <10<br>ab = $1.5 \times 10^2$ | pa = <10<br>ab = <10 |

As can be seen from Table 1, there is a pronounced antimicrobial effect from the 24FE3 beads extruded with the 2.0% w/w BG-Tec Plus antimicrobial agent. This has resulted in suppression of mould and bacterial growth in repeated use washing with these antimicrobial beads in apparatus as described in WO-A-2011/098815.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A method for cleaning a soiled substrate, said method comprising the treatment of a moistened soiled substrate with a formulation comprising a multiplicity of polymeric particles, wherein said polymeric particles comprise at least one antimicrobial agent, where said soiled substrate comprises leather or a textile fibre or fabric, and subsequently separating the polymeric particles from the substrate and recovering the polymeric particles in order to allow for re-use, wherein said antimicrobial agent is introduced into said polymer particles during extrusion of said polymer.

2. The method as claimed in claim 1, wherein said textile fibre or fabric is a natural or synthetic fibre or fabric, wherein said natural or synthetic fibre or fabric comprises cotton, nylon 6,6 or a polyester.

3. The method as claimed in claim 1, wherein said soiled substrate is wetted by contact with mains or tap water so as to achieve a substrate to water ratio of between 1:0.1 to 1:5 w/w.

4. The method as claimed in claim 1, wherein the ratio of said particles to the soiled substrate is in the range of from 0.1:1 to 10:1 w/w.

5. The method as claimed in claim 1, wherein said method comprises a batchwise process or continuous process and said treatment is carried out at a temperature of between 5° and 35° C. and/or for a duration of between 5 and 45 minutes.

6. The method as claimed in claim 1, wherein said antimicrobial agent comprises a solid chlorophenol derivative or a silver-containing material.

7. The method as claimed in claim 6, wherein said solid chlorophenol derivative comprises 5-chloro-2-(2,4-dichlorophenoxy)phenol or its derivatives.

8. The method as claimed in claim 6, wherein said silver-containing material comprises a silver-containing zeolite material.

9. The method as claimed in claim 1, wherein said antimicrobial agent is added to said polymer at a level of 0.1-5.0% (w/w).

10. The method as claimed in claim 1, wherein said formulation further comprises at least one additional cleaning agent.

11. The method as claimed in claim 10, wherein said at least one additional cleaning agent comprises at least one surfactant and said surfactant comprises at least one anionic, non-ionic, cationic, ampholytic, zwitterionic and/or semi-polar non-ionic surfactant.

12. The method as claimed in claim 11, wherein said at least one surfactant comprises at least one surfactant having detergent properties and said at least one additional cleaning agent comprises at least one detergent formulation.

13. The method as claimed in claim 11, wherein said at least one additional cleaning agent also comprises at least one enzyme and/or bleach.

14. The method as claimed in claim 11, wherein said at least one additional cleaning agent is mixed with said polymeric particles or is coated with said at least one additional cleaning agent.

15. The method as claimed in claim 12, wherein said detergent formulation additionally comprises at least one additive selected from anti-redeposition additives, optical brighteners, perfumes, softeners, builders, chelating agents, dye transfer inhibiting agents, dispersants, enzyme stabilizers, catalytic materials, bleach activators, polymeric dispersing agents, clay soil removal agents, suds suppressors, dyes, structure elasticizing agents, fabric softeners, starches, earners, hydrotropes, processing aids and/or pigments.

16. The method as claimed in claim 1, wherein said polymeric particles comprise polyalkenes, polyesters, polyamides or polyurethanes, or their copolymers, wherein said polyamide particles comprise nylon beads and wherein said nylon beads comprises Nylon 6,6 homopolymer having a molecular weight in the region of from 5000 to 30000 Daltons.

17. The method as claimed in claim 1, wherein said polymeric particles are in the shape of spheres, cubes or cylinders, and said particles are solid or hollow, wherein said cylindrically shaped particles optionally have an average particle diameter in the region of from 1.0 to 6.0 mm and the length of said particles is in the range of from 1.0 to 5.0 mm.

18. The method as claimed in claim 1, wherein said particles have an average mass in the region of from 1 to 50 mg.

19. The method as claimed in claim 1, wherein said polymeric particles comprise foamed or unfoamed polymeric materials and said polymers are either linear or crosslinked.

* * * * *